(12) United States Patent
Daft et al.

(10) Patent No.: US 6,245,016 B1
(45) Date of Patent: Jun. 12, 2001

(54) ULTRASOUND IMAGING SYSTEM HAVING POST-BEAMFORMER SIGNAL PROCESSING USING DECONVOLUTION ALGORITHM

(75) Inventors: Christopher Mark William Daft, Schenectady, NY (US); Mark Robert Luettgen, Winchester; Robert Ronald Tenney, Andover, both of MA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/266,883

(22) Filed: Mar. 12, 1999

(51) Int. Cl.[7] .............................. A61B 8/00; A61B 8/06
(52) U.S. Cl. ............................................... 600/443
(58) Field of Search .................... 600/437, 443, 600/447, 454–456; 382/254, 260–265, 274, 276–279

(56) References Cited

U.S. PATENT DOCUMENTS

| | | | |
|---|---|---|---|
| 5,442,462 | * 8/1995 | Guissin | 358/468 |
| 5,550,935 | * 8/1996 | Erderme et al. | 382/260 |
| 5,561,611 | * 10/1996 | Avinash | 364/553 |
| 5,860,930 | * 6/1999 | Guvocar | 600/455 |
| 5,919,139 | * 7/1999 | Lin | 600/443 |

OTHER PUBLICATIONS

Kotropoulos et al., "Optimum nonlinear signal detection and estimation in the presence of ultrasonic speckle", Ultrasonic Imaging, vol. 14, pp. 249–275 (1992).

Loupas et al. "An adaptive weighted median filter for speckle suppression in medical ultrasonic images", IEEE Trans. on Circuits and Systems, vol. 36, pp. 129–135 (1989).

Koo et al., "Speckle reduction with edge preservation in medical ultrasonic images using a homogeneous region growing mean filter", Ultrasonic Imaging, vol. 13, pp. 211–237 (1991).

Bamber et al., "Adaptive filtering for reduction of speckle in ultrasonic pulse–echo images", Ultrasonics, vol. 24, pp. 41–44 (1986).

Dutt et al., "Adaptive speckle reduction filter for log–compressed B–scan images", IEEE Trans. on Med. Imag., vol. 15, pp. 802–813 (1996).

(List continued on next page.)

*Primary Examiner*—Francis J. Jaworski
(74) *Attorney, Agent, or Firm*—Marvin Snyder; Douglas E. Stoner (57) ABSTRACT

A post-beamformer signal processing algorithm is utilized in a system for improving ultrasound B-scan resolution and contrast. The algorithm is based on a model of the imaging process that represents: 1) the shape of the pulse transmitted by the transducer and the frequency-dependent attenuation of that pulse as it propagates through tissue and back to the transducer; and 2) the effects of changes in frequency-dependent attenuation and in scatterer density as the pulse propagates across tissue boundaries and through cystic and calcified structures. The system provides substantial improvements in resolution and contrast as compared to standard envelope-detected imagery.

26 Claims, 5 Drawing Sheets

OTHER PUBLICATIONS

Jensen, "A model for the propagation and scattering of ultrasound in tissue", J. Acoust. Soc. Am., vol. 89, pp. 182–190 (1990).

Liu et al., "Digital processing for improvement of ultrasonic abdominal images", IEEE Trans. Med. Imag., vol. 2, pp. 66–75 (1983).

Kuc, "Application of Kalman filtering techniques to diagnostic ultrasound", Ultrasonic Imaging, vol. 1, pp. 105–120 (1979).

Hokland et al., "Markov models of specular and diffuse scattering in restoration of medical ultrasound images", IEEE Trans. Medical Imaging, vol. 43, pp. 660–669 (1996).

Mendel et al., "New fast optimal white noise estimators for deconvolution", IEEE Trans. Geosci. Electr., vol. 15, pp. 32–41 (1977).

van der Veen et al., "Subspace–based signal analysis using singular value decomposition", IEEE Proc., vol. 81, pp. 1277–1310 (1993).

Howard, "System analysis of Semi–Markov processes," IEEE Trans. Mil. Electr., pp. 114–124 (1964).

Tugnait, "Detection and estimation for abruptly changing systems," Automatica, vol. 18, pp. 607–615 (1982).

Pattipati et al., "A unified view of state estimation in switching environments," American Control Conf., San Francisco, California, pp. 458–465, Jun. (1993).

Kurien, "Issues in the design of multitarget tracking systems," in: Multitarget–Multisensor Tracking, Y. Bar–Shalom (ed.), Artech House, Norwood, Massachusetts (1990).

Maragos et al., "Morphological filters, Part 1: Their set–theoretic analysis and relations to linear shift invariant filters," IEEE Trans. Acoust. Speech, Sig. Proc., vol. 35, No. 8, pp. 1153–1169 (1987).

Maragos et al., "Morphological filters, Part 2: Their relations to median, order–statistic, and stack filters," IEEE Trans. Acoust., Speech, Sig. Proc., vol. 35, No. 8, pp. 1170–1184 (1987).

* cited by examiner

ULTRASOUND IMAGING SYSTEM HAVING POST-BEAMFORMER SIGNAL PROCESSING USING DECONVOLUTION ALGORITHM

FIELD OF THE INVENTION

This invention relates to ultrasound imaging of the human anatomy for the purpose of medical diagnosis and, more particularly, to methods and apparatus for imaging fluid or tissue in the human body by transmitting ultrasound waves into the fluid or tissue and then detecting ultrasound echoes reflected therefrom.

BACKGROUND OF THE INVENTION

Conventional ultrasound scanners are capable of operating in different imaging modes, such as B mode and color flow mode. In the B mode, two-dimensional images are generated in which the brightness of a display pixel is based on the intensity of the echo return.

In conventional ultrasound imaging operating in B mode, an ultrasound transducer array transmits a series of multi-cycle (typically 2 or 3 cycles) tone bursts which are focused at different transmit focal positions, while dynamic receive delays are applied. These tone bursts are fired at a pulse repetition frequency (PRF) that is typically in the kilohertz range. Each transmit beam propagates through the object being scanned and is reflected by ultrasound scatterers in the object. The returned radio frequency (RF) signals are detected by the elements of the transducer array and then transformed into in-phase and quadrature (I/Q) components and formed into a receive beam. The transformation into I/Q components is accomplished by bandpass filtering either the separate RF signals in the receive channels or the beamsummed RF signal. The I/Q components are then shifted down in frequency and sent to a B-mode processor which incorporates a detector, e.g., an envelope detector, for forming the envelope of the beamsummed receive signal by computing the quantity $(I^2+Q^2)^{1/2}$. The envelope of the signal undergoes some additional B-mode processing, such as logarithmic compression, to form display data that are interpolated by a scan converter into X–Y format for video display. A video processor maps the video data to a gray scale or mapping for video display and sends the gray scale image frames to a video monitor for display.

The safety, versatility and real-time capability of ultrasound imaging equipment has made it an extremely valuable diagnostic tool. However, due to frequency-dependent pulse attenuation, the non-stationary point spread functions of the imaging systems, and the coherent nature of the ultrasound imaging process, is B-mode images have poor resolution and contrast in comparison to other medical imaging modalities, such as computed tomography and magnetic resonance imaging, and contain significant speckle that masks tissue structure at smaller scales. There are two ways to deal with these problems—process more data in generating a single image through techniques such as frequency or spatial compounding, or do more processing at the back-end of the beamformer to take advantage of known tissue characteristics and spatial correlation, in the underlying reflectivity profile. The former can improve ultrasound imagery at the expense of increased system complexity and lower frame rate, whereas the latter can improve it at the expense of increased computational load.

Known post-beamformer signal processing methods for enhancing B-mode imagery can be divided into two groups, depending on whether they process the beamformer signal directly or the envelope-detected imagery.

Representative examples of methods in the latter class include the nonlinear filtering method described in Kotropoulos et al., "Optimum Nonlinear Signal Detection and Estimation in the Presence of Ultrasonic Speckle", Ultrasonic Imaging, vol. 14, pp. 249–275 (1992), in which a multiplicative noise model is used to derive a local estimator of signal intensity; the adaptive methods in Loupas et al. "An Adaptive Weighted Median Filter for Speckle Suppression in Medical Ultrasonic Images", IEEE Trans. on Circuits and Systems, Vol. 36, pp. 129–135 (1989), and Koo et al., "Speckle Reduction with Edge Preservation in Medical Ultrasonic Images Using a Homogeneous Region Growing Mean Filter", Ultrasonic Imaging, Vol. 13, pp. 211–237 (1991), in which the window size of median and averaging filters are set based on similarity of local statistics; the adaptive filtering method in Bamber et al., "Adaptive Filtering For Reduction Of Speckle In Ultrasonic Pulse-Echo Images", Ultrasonics, Vol. 24, pp. 41–44 (1986), in which the degree of smoothing is dependent on a statistic quantifying the degree of speckle formation; and the related approach in Dutt et al., "Adaptive Speckle Reduction Filter For Log-Compressed B-Scan Images", IEEE Trans. on Med. Imag., Vol. 15, pp. 802–813 (1996), in which the log-compressed imagery is filtered. While these methods generally result in images in which speckle is significantly reduced, they typically do not provide significant contrast or resolution improvement, and in many cases result in images of substantially reduced resolution.

On the other hand, methods based on processing the beamformer signal directly, typically referred to as deconvolution methods, can result in resolution improvement if adequate prior system information can be obtained. The methods are generally based on a one-dimensional or two-dimensional convolutional model of the beamformer signal acquisition process, e.g., $$y(t)=h(t)*w(t)+v(t) \qquad (1)$$

where y(t) is the beamformer output, h(t) is the pulse response of the imaging system (including the transducer pulse along with the axial and/or lateral impulse response of the transducer itself), w(t) is the underlying tissue reflectance (usually assumed to be a white noise process), and v(t) is additive white noise. Convolutional models can be justified by assuming weak scattering (no bones or air pockets), single scattering (no reverberations or multipath reflections) and no absorption (see Jensen, "A Model For The Propagation And Scattering Of Ultrasound In Tissue", J. Acoust. Soc. Am., Vol. 89, pp. 182–190 (1990), for discussion and references). The improved resolution is obtained because additional system information—including the intensity of the additive noise v(t) and reflection sequence w(t) and the pulse response h(t)—is exploited. While the resulting algorithms are typically not highly sensitive to parameter mismatch, reasonable parameter estimates are required to obtain significant increases in resolution and, just as important from a clinician's perspective, to avoid the introduction of spurious artifacts, especially at tissue boundaries.

Deconvolution filters generally have one or more of the following limitations:

(1) Such filters are depth invariant or piecewise invariant and as a result do not take into account the depth-varying structure of the transducer impulse response resulting from frequency-dependent pulse attenuation and transducer dynamic focusing and aperture effects. Wiener filtering approaches such as that in Liu et al., "Digital Processing For Improvement Of Ultrasonic Abdominal Images", IEEE Trans. Med. Imag., Vol. 2, pp. 66–75 (1983), and Hoess et al., "Adaptive Wiener Filtering For B-Mode Image Improvement", IEEE Ultrasonics Symposium, pp. 1219–1222 (1992), are explicitly based on a depth-invariant pulse response, and are typically applied by first segmenting the data and then applying the filter to each segment separately. The Kalman filtering methods proposed in Jensen, "Deconvolution Of Ultrasound Images", Ultrasonic Imaging, Vol. 14, pp. 1–15 (1992) (see also Kuc, "Application Of Kalman Filtering Techniques To Diagnostic Ultrasound", Ultrasonic Imaging, Vol. 1, pp. 105–120 (1979)), allow for continuously depth-varying pulse responses; however the authors do not take advantage of this because they estimate their pulses directly from the data using windows of fixed size and spacing.

(2) Deconvolution filters do not take into account abrupt changes in attenuation and scattering characteristics across tissue boundaries. In the Jensen and Hoess papers cited above, variations in scatterer density and strength and pulse attenuation are accounted for by estimating filter parameters and processing data over preselected windows. This methodology provides some degree of adaptivity, but does not fully address the problem since the preselected windows are almost always inconsistent with the actual tissue boundaries.

(3) Deconvolution filters process A-lines independently, thereby failing to take advantage of the significant spatial correlation in tissue type. This is true of methods such as those described in the Liu et al., Jensen and Kuc papers cited above.

(4) Deconvolution filters often cannot realistically be implemented in real-time hardware. The Wiener and Kalman filtering approaches described in the Liu et al., Jensen and Hoess papers could be implemented in real-time, but Markov random field-based approaches such as those in Hokland et al., "Markov Models Of Specular And Diffuse Scattering In Restoration Of Medical Ultrasound Images", IEEE Trans. Medical Imaging, Vol. 43, pp. 660– 669 (1996), while fully addressing the issues above, are far too computationally intensive to implement in real-time.

Thus there is need for a post-beamformer signal processing technique using a deconvolution approach that overcomes the foregoing limitations.

SUMMARY OF THE INVENTION

An ultrasound imaging system utilizes a post-beamformer signal processing algorithm for improving ultrasound B-scan a resolution and contrast. The algorithm is based on a model of the imaging process that represents: 1) the shape of the pulse transmitted by the transducer and the frequency-dependent attenuation of that pulse as it propagates through tissue and back to the transducer; and 2) the effects of changes in frequency-dependent attenuation and in scatterer density as the pulse propagates across tissue boundaries and through cystic and calcified structures. The algorithm provides substantial improvements in resolution and contrast as compared to standard envelope-detected imagery.

The system employs a deconvolution algorithm which is based on a convolutional model that generalizes Eq. (1) and explicitly allows for depth-varying pulse responses (as well as tissue type changes). The pulse shape at each point in the tissue is computed using a model cognizant of all of the imager's parameters, e.g. element impulse response, aperture size, windowing, etc.

The generalization of the convolutional model takes into account the changes in reflection sequence density and tissue attenuation that occur at tissue boundaries through the use of a set of discrete states, one for each tissue type, along with a Markov or Semi-Markov model that describes transitions between those states. This discrete state component of the model allows capture, in a statistically meaningful way, of the changes in tissue type with depth.

The system takes advantage of two-dimensional correlation in the tissue structure by computing an estimate of tissue type as a function of position using a two-phase approach. In the first phase, a maximum a posteriori (MAP) estimate of tissue type is computed for each A-line independently. In the second phase, the tissue type estimates are post-processed with a two-dimensional morphological filter to eliminate isolated errors. This two-phase approach is sub-optimal as compared to the single-phase, fully two-dimensional approach described in the Hokland et al. paper, but can be implemented in real-time and produces high-quality, spatially coherent tissue type estimates.

A Kalman filter-type algorithm is employed to compute the MAP tissue estimate and a similar algorithm developed in Mendel et al., "New Fast Optimal White Noise Estimators For Deconvolution", IEEE Trans. Geosci. Electr., Vol. 15, pp. 32–41 (1977), is employed to compute the optimal reflection sequence estimates, given the tissue type estimate. These algorithmic structures and the morphological filtering are extremely efficient and can be implemented in real-time hardware.

DETAILED DESCRIPTION OF THE PREFERRED EMBODIMENT

Figure 1:
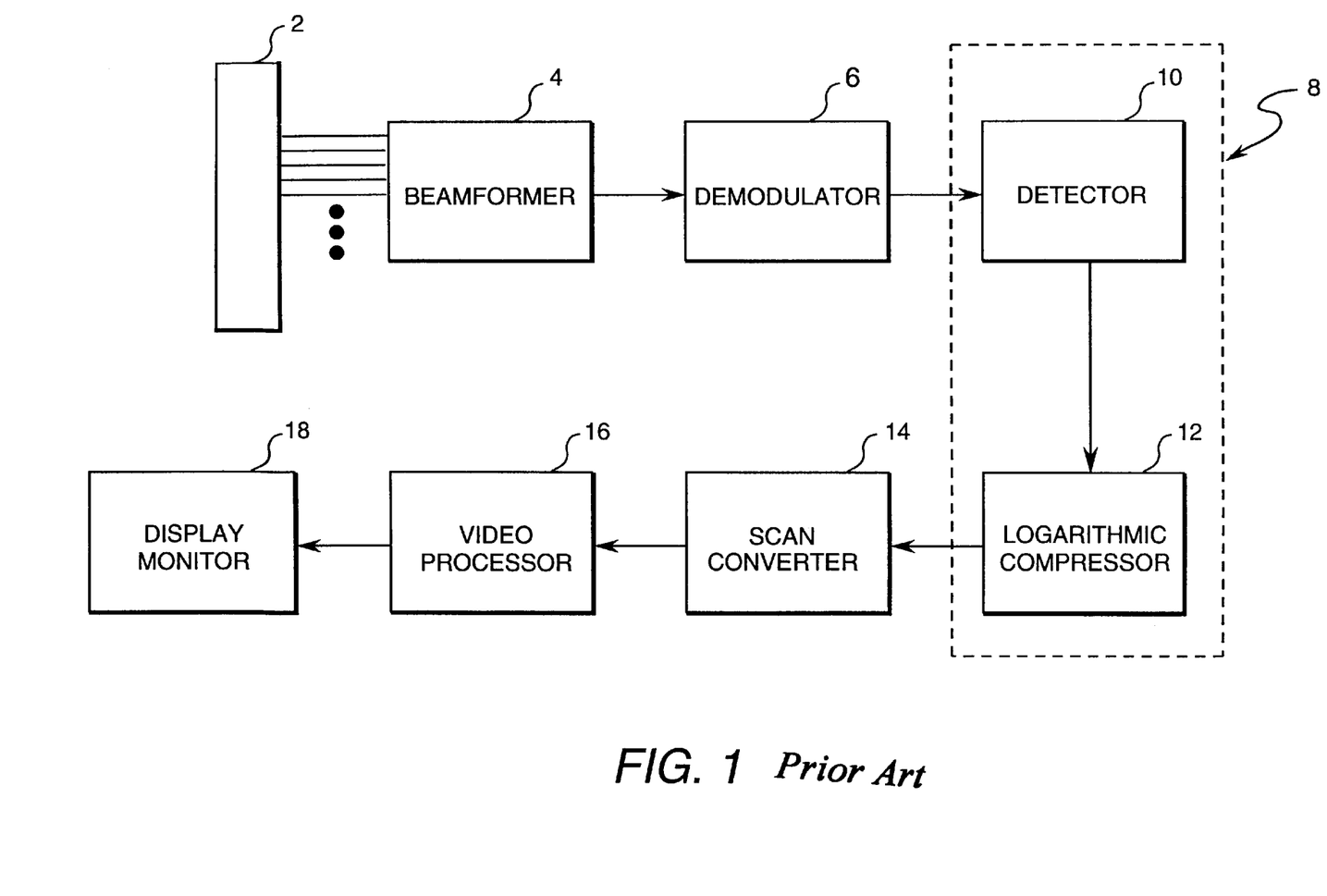
FIG. 1 is a block diagram showing the major functional subsystems within a conventional real-time ultrasound imaging system.

In a conventional ultrasound imaging system (shown in FIG. 1), an ultrasound transducer array 2 is activated to transmit a series of multi-cycle (typically 2 or 3 cycles) tone bursts which are focused at various transmit focal positions with dynamic receive focusing. These tone bursts are fired at a pulse repetition frequency (PRF) that is typically in the kilohertz range. Each transmit beam propagates through the object being scanned and is reflected by ultrasound scatterers in the object. The returned RF signals are detected by the elements of the transducer array and transformed into in-phase and quadrature (I/Q) components. The I/Q components are formed into a receive beam by a beamformer 4. The transformation into I/Q components is accomplished by bandpass filtering either the separate RF signals in the receive channels responsive to transducer array 2, or the beamsummed RF signal. The I/Q components are then shifted down in frequency by a demodulator 6. The downshifted I/Q components are then sent to a B-mode processor 8, which includes a detector 10, e.g., an envelope detector for forming the envelope of the beamsummed receive signal by computing the quantity $(I^2+Q^2)^{1/2}$. The envelope of the signal undergoes some additional B-mode processing, such as logarithmic compression by a logarithmic compressor 12, to form display data which are supplied to a scan converter 14 that converts the display data into X–Y format for video display. The scan-converted frames are passed to a video processor 16, which maps the video data to a gray scale or mapping for video display. The gray scale image frames are then sent to a video monitor 18 for display.

Figure 2:
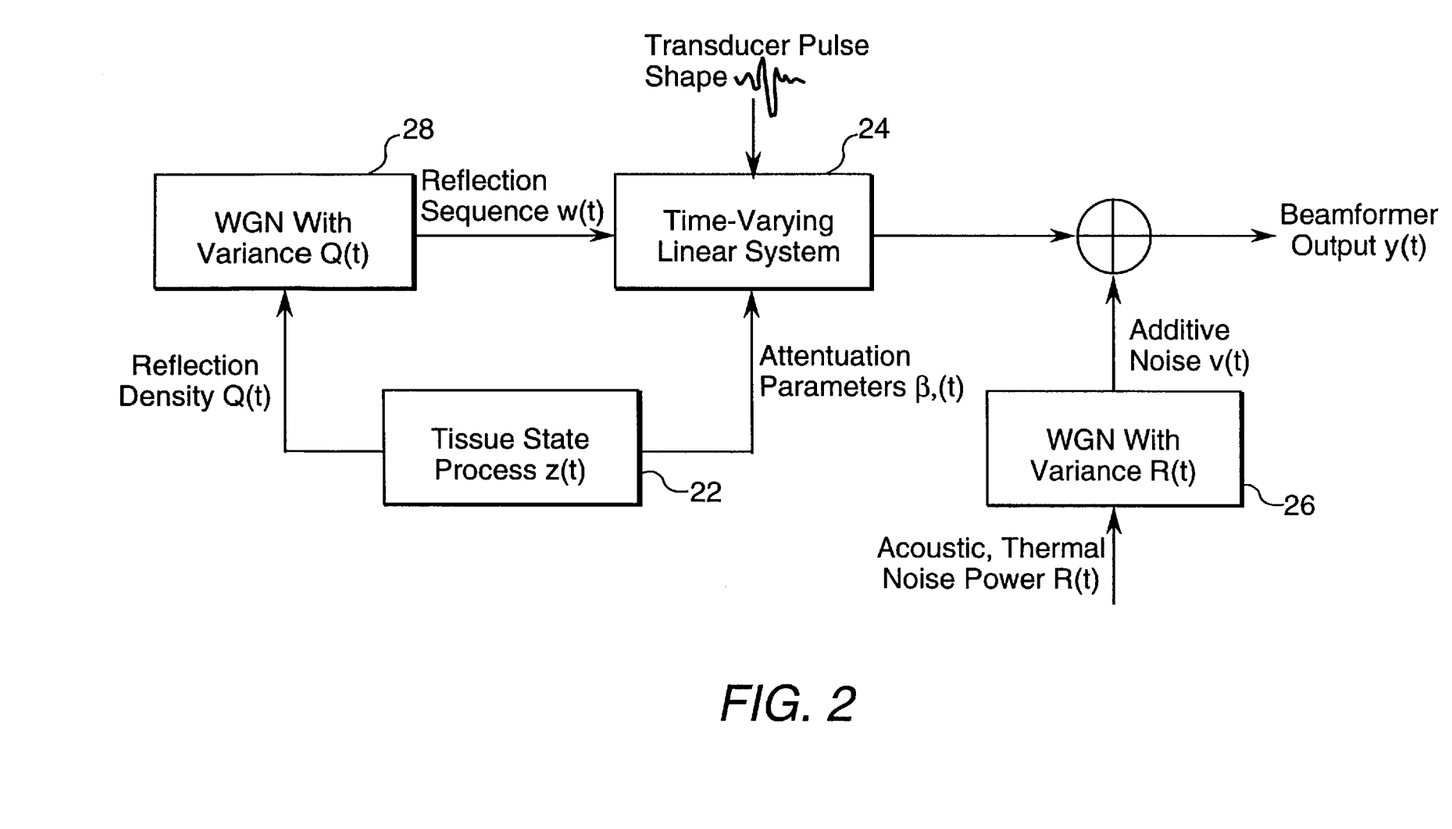
FIG. 2 is a block diagram of an imaging system model in accordance with a preferred embodiment of the invention.

The method by which the invention operates may be modeled as shown in FIG. 2. This model is a generalization of the convolutional model discussed in the previously cited publications of Jensen, and is based on two main ideas.

First, the invention employs a discrete state model that represents knowledge about how tissue scattering strength and attenuation properties change with depth. Mathematically, the model defines the statistics of a discrete random process representing tissue type as a function of position. Associated with each tissue type is a set of parameters that defines the tissue reflectance strength and the tissue attenuation properties.

Second, the invention utilizes a continuous state model that presents the beamformer output signal as the convolution of the tissue reflection sequence and the depth-varying transducer pulse plus noise. This model is represented in a state-space form that allows for the development of efficient reflection sequence estimation algorithms.

In particular, the imaging system utilizes an algorithm for estimating the reflection sequence using the beamformer measurements that is near-optimal for the hybrid discrete-continuous state imaging system model. The algorithm is based on the combination of a Kalman filtering algorithm for computing tissue estimates and a smoothing algorithm for computing reflection sequence estimates.

Tissue type changes with depth. To model this characteristic, the preferred embodiment of the invention uses discrete state Markov and Semi-Markov models. Discrete state Markov models are made up of a set of states, e.g., "soft tissue", "cyst" and "wire", along with values for the probabilities of transitioning from one state to another at each sample point p(i|j), where i and j are states. Markov and Semi-Markov models provide a very general framework for representing prior information about tissue state changes and, as discussed hereinafter, lead to extremely efficient Kalman filtering-type algorithms for likelihood calculation and reflection sequence estimation. As shown in FIG. 2, the discrete state model defines the statistics of the tissue state process z(t) 22 and, through the tissue state at each beamformer sampling point t, defines the corresponding reflection density Q(t) and attenuation parameters β and γ.

Figure 3:
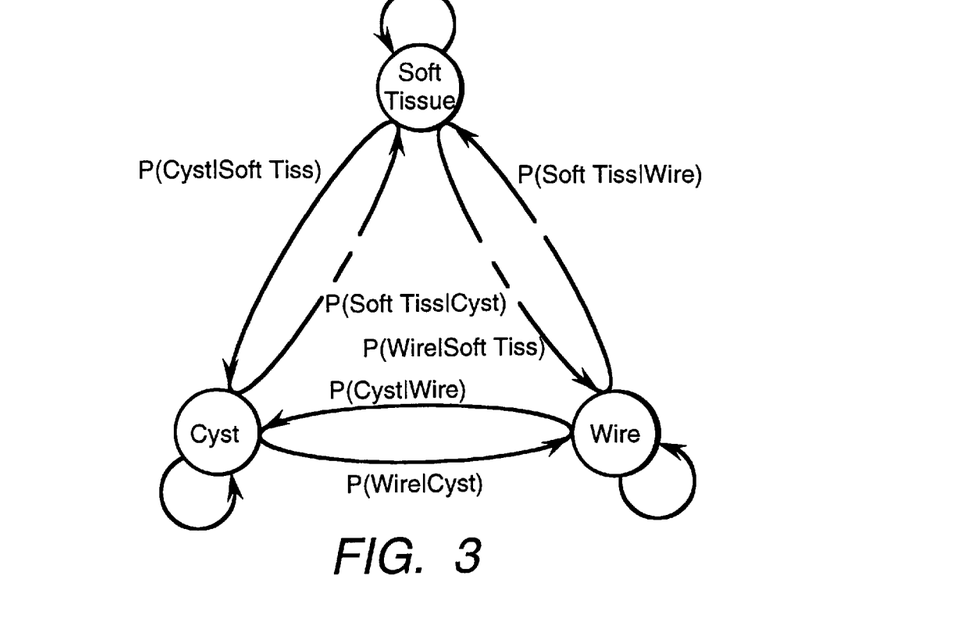
FIG. 3 is a graphical representation of a Markov discrete state model of tissue type changes used in phantom experiments.

One example of a discrete state Markov model used in phantom experiments is represented graphically in FIG. 3. The model includes the three states mentioned above plus transition probabilities that reflect prior information about the phantom, namely that: 1) transitions into "wire" states are very improbable because there are only a few wires in the phantom; 2) having transitioned into a wire, it is very likely that there will soon be a transition out of the wire, because wires are small; and 3) cysts and soft tissue both cover significant portions of the phantom (at least the portion of the phantom shown in FIG. 3). This information suggests that transition probabilities into the wire state from cyst and soft tissue should be small, the transition probabilities into cyst and soft tissue from wire should be large, and the transition probabilities to and from cyst and tissue states should be equal. The parameters for this and other models are set based on intuition of this sort.

Figure 4:
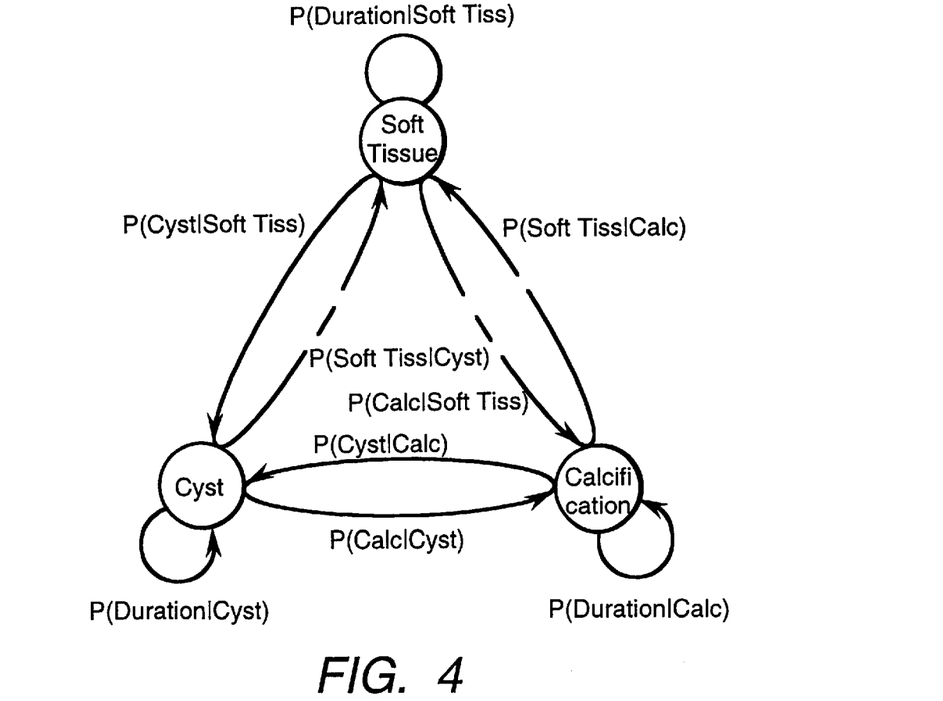
FIG. 4 is a graphical representation of a Semi-Markov generalization proposed for in-vivo imaging of tissue.

In practice, technicians will not have the time or knowledge required to set the transition probabilities on-line, so the system must be able to use information in the beamformer data itself and from the technician at the level of "this is a transrectal prostate scan" to fix the parameters. It is practicable to generate good estimates of tissue parameters from the ultrasound system's control settings. Most valuably, time gain control slider settings (when adjusted for a uniform image) will indicate the depth dependence of the attenuation, Semi-Markov models provide a substantial generalization of Markov models. Specifically, Markov models are limited to geometric probability distributions (and convolutions of these) for state dwell times, whereas Semi-Markov models allow for arbitrary dwell time probability distributions. For instance, in a Semi-Markov model one might use a probability distribution for cyst dwell time that reflects knowledge about the minimum and maximum cyst diameters that one can reasonably expect to encounter. Allowing for arbitrary dwell time distributions provides the flexibility to take advantage of knowledge such as this very easily. For example, one can use the Semi-Markov model shown in FIG. 4 for a prostate imaging application, with probability distributions for the dwell times to be developed based on discussions with clinical consultants.

The number of states in the Markov and Semi-Markov models used in the invention is not limited to three. For instance, the "soft tissue" state could be separated into "peripheral zone", "transitional zone", "fibromuscular stroma" and "urethra" states for a prostate imaging application.

The time-varying linear system 24 (FIG. 4) that operates on the reflection sequence represents the transmitted waveform, the transducer impulse response, the frequency-dependent tissue attenuation, the receiver impulse response and additive noise in the receiver 26 (FIG. 2). This system is represented in state-space form, with the reflection sequence w(t) corresponding to the input signal and the beamformer signal y(t corresponding to the output signal, as follows:

$$x(t)=A(t-1)x(t-1)+B(t-1)w(t-1)$$
$$y(t)=C(t)x(t)+v(t) \qquad (2)$$

defined over t=1, 2, . . . , T, with v(t) being a Gaussian random variable with covariance R(t), and with x(1)=0 (the system is initially at rest). The first of Eqs. (2) is the state equation and the second is the measurement equation. Physically, the reflection sequence corresponds to perturbations in average tissue density and intrinsic sound propagation velocity and can take on both positive and negative values. The reflection sequence is modeled as a white Gaussian noise (WGN) process 28 (FIG. 2) with a depth-dependent variance given by a tissue reflectivity density function Q(t), which is the product of scatterer density and average scattering power. The tissue type sequence z(τ), τ=1, 2, . . . , t, defines the state space parameters A(τ), B(τ), C(τ+1) and Q(τ), for τ=1, 2, . . . , t. These parameters and the noise covariance R(t) for this model are chosen as follows.

In accordance with a preferred embodiment of the invention, parameters A(t), B(t) and C(t) respectively represent the transducer point spread function, the transmitted pulse shape and the frequency-dependent attenuation. It is assumed that the pulse attenuation is equal to $\beta f^\gamma d$ dB at frequency f and depth d, wherein $\beta$ and $\gamma$ are attenuation parameters. This is a standard attenuation model with typical soft tissue values for $\beta$ ranging from 0.3 to 1.5. The soft tissue value of $\gamma$ is approximately 1. Given these parameters for each tissue type, comprehensive ultrasound imager simulation is used to generate the pulse shape at each sampling depth. Given these pulses computed by the comprehensive ultrasound imager simulation, the methodology described in van der Veen et al., "Subspace-Based Signal Analysis Using Singular Value Decomposition", IEEE Proc., Vol. 81, pp. 1277–1310 (1993) (the contents of which are incorporated by reference herein), is used to compute approximate state-space parameters A(t), B(t) and C(t).

In the preferred embodiment of the invention, the parameter R(t) represents the acoustic, thermal and round-off error noise power. This parameter is estimated using water tank tests and transducer design analysis.

The parameter Q(t) represents the reflection sequence covariance. This parameter is estimated for each tissue type using data from the medium being interrogated. Like the tissue transition probabilities, technicians will not have the time or knowledge required to set this parameter on-line, so the system must use information in the beamformer data itself and from the technician at the level of "this is a transrectal prostate scan" to fix the parameter.

Figure 5:
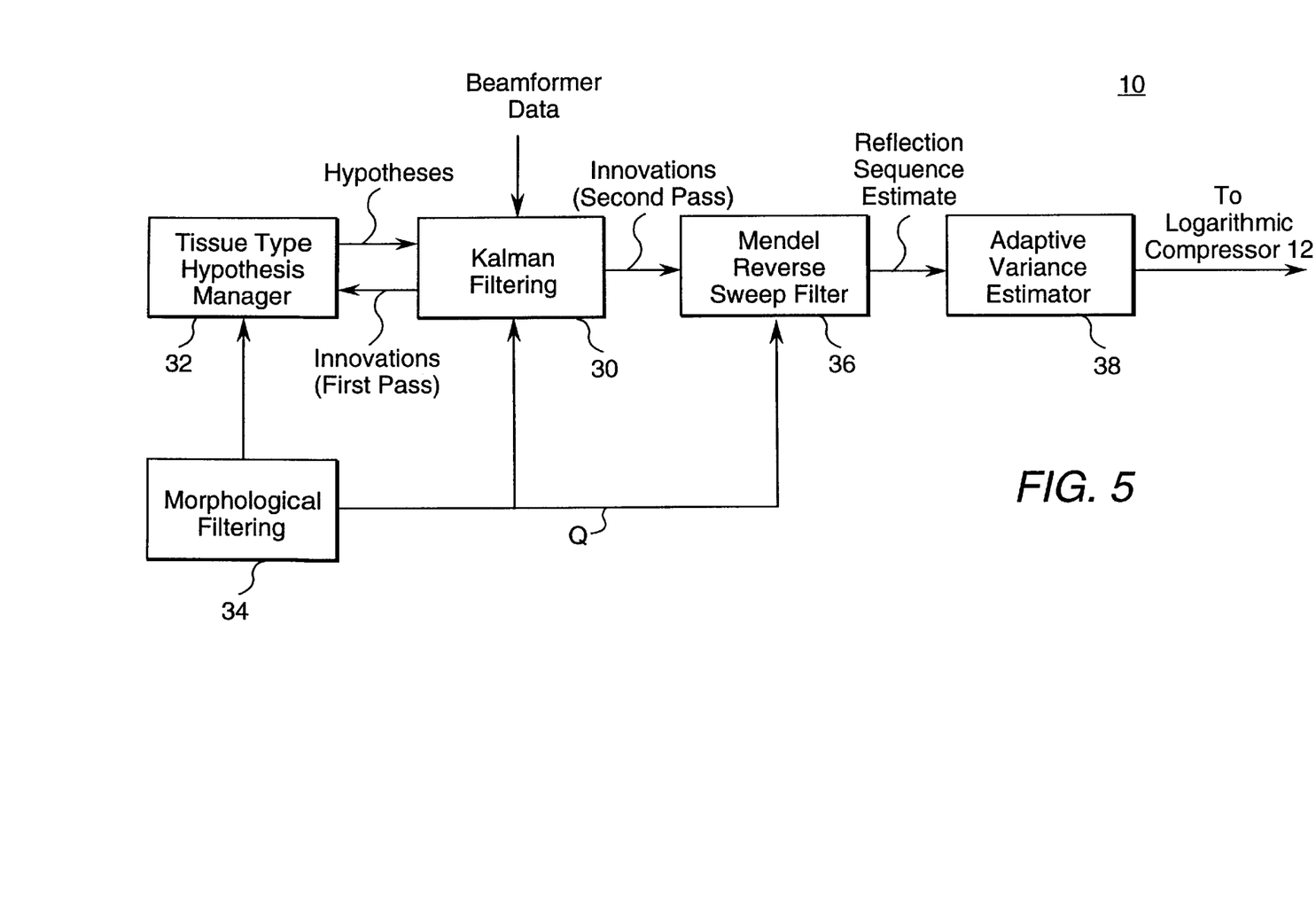
FIG. 5 is a block diagram showing the components of an optimal detector in accordance with a preferred embodiment of the invention.

In a preferred embodiment of the invention, detector 10 (FIG. 1) is an optimal detector instead of an envelope detector. The optimal detector as depicted in FIG. 5, comprises: a bank of Kalman filters 30 which receive the beamformer RF output signal and compute innovations in accordance with different tissue type sequence estimates or hypotheses; a tissue type hypothesis manager 32 which generates hypotheses and selects the optimal hypothesis based on likelihoods computed from the innovations produced by the Kalman filters; a morphological filter 34 which receives the optimal hypothesis for each A-line from the tissue type hypothesis manager 32 and filters the optimal hypotheses to eliminate spurious errors so that the filtered hypotheses can be used by the Kalman filters to recompute the innovations; a Mendel reverse sweep filter 36 which receives the recomputed innovations and the filtered optimal hypotheses and computes reflection sequence estimates for each A-line; and an adaptive variance estimator 38 which computes a variance estimate from each reflection sequence estimate to form respective deconvolved A-lines which are supplied to the logarithmic compressor 12, shown in FIG. 1.

The optimal estimation algorithm in accordance with a preferred embodiment of the invention takes as input beamformer measurements $y^t = \{y(1), y(2), \ldots, y(t)\}$ (referred to as "reflection data samples") for a single A-line, and produces an estimate of the associated reflection sequence $w^t = \{w(1), w(2), \ldots, w(t)\}$. Ideally, one would like to compute the Bayesian estimate of $w^{T-1}$ given $y^T$, which is optimal in the sense that it minimizes the mean square estimation error and which is given by the conditional expectation $E(w^{T-1}|y^T)$. This is difficult to do directly because the measurements also depend on the tissue type process $z^t = \{z(1), z(2), \ldots, z(t)\}$. The starting point for the optimal estimation algorithm is a decomposition of the expectation given by:

$$E(w^{T-1}|y^T) = \Sigma_{Z^{T-1}} E(w^{T-1}|y^T, z^{T-1}) p(Z^{T-1}|y^T) \quad (3)$$

where $p(z^{T-1}|y^T)$ is the conditional probability based on all beamformer measurements of a particular tissue type sequence, $E(w^{T-1}|y^T, z^{T-1})$ is the expectation of the reflection sequence, conditioned on both the beamformer measurements $y^T$ and the tissue type sequence $z^{T-1}$, and $Z^{T-1}$ is a set consisting of all possible tissue type sequences $z^{T-1}$.

The value of $E(w^{T-1}|y^T, z^{T-1})$ for a particular set of beamformer measurements, additive noise covariance R(t) and tissue type sequence (or, equivalently, the beamformer measurements, R(t) and the parameters A(t), B(t), C(t) and Q(t) in Eqs. (2)) can be computed using an algorithm developed by Mendel et al. in "New Fast Optimal White Noise Estimators For Deconvolution," IEEE Trans. Geosci. Electr., Vol. 15, pp. 32–41 (1977), the contents of which are incorporated by reference herein.

The conditional probability $p(z^{T-1}|y^T)$ can be computed from:

$$p(z^{T-1}|y^T) = p(y^T|z^{T-1})p(z^{T-1})/p(y^T) \quad (4)$$

The term $p(z^{T-1})$ is simple to compute for the Markov and Semi-Markov type models (see Howard, "System Analysis Of Semi-Markov Processes," IEEE Trans. Mil. Electr., pp. 114–124 (1964), the contents of which are incorporated by reference herein) used to model the tissue type process. The term $p(y^T|z^{T-1})$ can be computed recursively as follows:

$$p(y^t|z^{t-1}) = p(y(t)|y^{t-1}, z^{t-1}) p(y^{t-1}|z^{t-1}) \quad (5)$$
$$= p(y(t)|y^{t-1}, z^{t-1}) p(y^{t-1}|z^{t-2})$$

where the first equality follows from Bayes' rule and the second equality follows from the independence of y(t−1) and z(t−1). These recursive calculations can be performed using a Kalman filter (see Jazwinsky, Stochastic Processes and Filtering Theory, Academic Press (1970)).

In principle, the term $p(y^T)$ in Eq. (4) can then be computed as follows:

$$p(y^T) = \Sigma_{z^{T-1}} p(y^T|z^{T-1}) p(z^{T-1}) \quad (6)$$

In practice, this is not possible because the cardinality of the set $Z^{T-1}$ is equal to $N^{T-1}$, where N is the number of states. Thus, the expectation in Eq. (3) cannot be computed exactly. Instead, one must settle for an approximation of it and the most natural method to obtain such an approximation of the expectation is to compute the conditional probabilities $p(z^{T-1}|y^T)$ recursively, keeping track of only a relatively small number of hypotheses at each step. There are many approaches available for choosing which hypotheses to keep because hybrid state models of this sort are widely used in the control community to address related problems in fault detection, state estimation under uncertain observations and tracking (see Tugnait, "Detection And Estimation For Abruptly Changing Systems," Automatica, Vol. 18, pp. 607–615 (1982) and Pattipati et al., "A Unified View Of State Estimation In Switching Environments," American Control Conf., San Francisco, Calif., pp. 458–465, June (1993) for surveys of the available approaches; see also Kurien, "Issues In The Design Of Multitarget Tracking Systems," in: Multitarget-Multisensor Tracking, Y. Bar-Shalom (ed.), Artech House, Norwood, Mass. (1990)). The approach adopted for the present invention is based on a simple method in which, at each step, the top K hypotheses are kept, i.e., those hypotheses with the highest likelihood $p(y^T|z^{T-1}) p(z^{T-1})$.

The likelihood $p(y^T|z^{T-1})p(z^{T-1})$ is computed as follows. Because the invention employs a Markov model for the discrete-state tissue type model, $p(z^{T-1})$ is equal to the product of the tissue model transition probabilities $p(z(t)|z(t-1))$ over the range of the time indices, $t=1, \ldots, (T-1)$, with $p(z(1)|z(0))$ set equal to the a priori probability of $p(z(1))$. in mathematical terms:

$$p(z^{T-1}) = \prod_{t=1}^{T-1} p(z(t) \mid z(t-1)) \tag{7}$$

Note that this can be computed recursively using the formula:

$$p(z^{t-1}) = p(z(t-1)z(t-2))p(z^{t-2}) \tag{8}$$

Because the invention employs a state space model of the form in Eq. (2), $p(y^T|z^{T-1})$ is equal to the product of the probability densities of the innovations values over the range of the time indices, $t=1, \ldots, (T-1)$. In mathematical terms:

$$p(y^T \mid z^{T-1}) = \prod_{t-1}^{T} \frac{1}{(2\pi \ det(V(t)))^{1/2}} \exp\left\{-\frac{1}{2} v(t) V^{-1}(t) v(t)\right\} \tag{9}$$

where $V(t)$ is the covariance of $v(t)$ and is computed as $$V(t) = C(t)P(t|t-1)C^T(t) + R(t) \tag{10}$$

is where $C(t)$ and $R(t)$ are parameters in the state space model, and the formula for $P(t|t-1)$ is given in Eq. (5). Additionally, $p(y^T|z^{T-1})$ can be computed recursively using the formula:

$$p(y^t \mid z^{t-i}) = \frac{1}{(2\pi \ det(V(t)))^{1/2}} \exp\left\{-\frac{1}{2} v(t) V^{-1}(t) v(t)\right\} p(y^{t-1} \mid z^{t-2}) \tag{11}$$

By combining the recursive equations in Eqs. (8) and (11), an overall recursive formula for the likelihood $p(y^T|z^{T-1})p(z^{T-1})$ can be obtained. This recursive method is implemented in the deconvolution algorithm design of a preferred embodiment of the invention, due to its efficiency.

Figure 6:
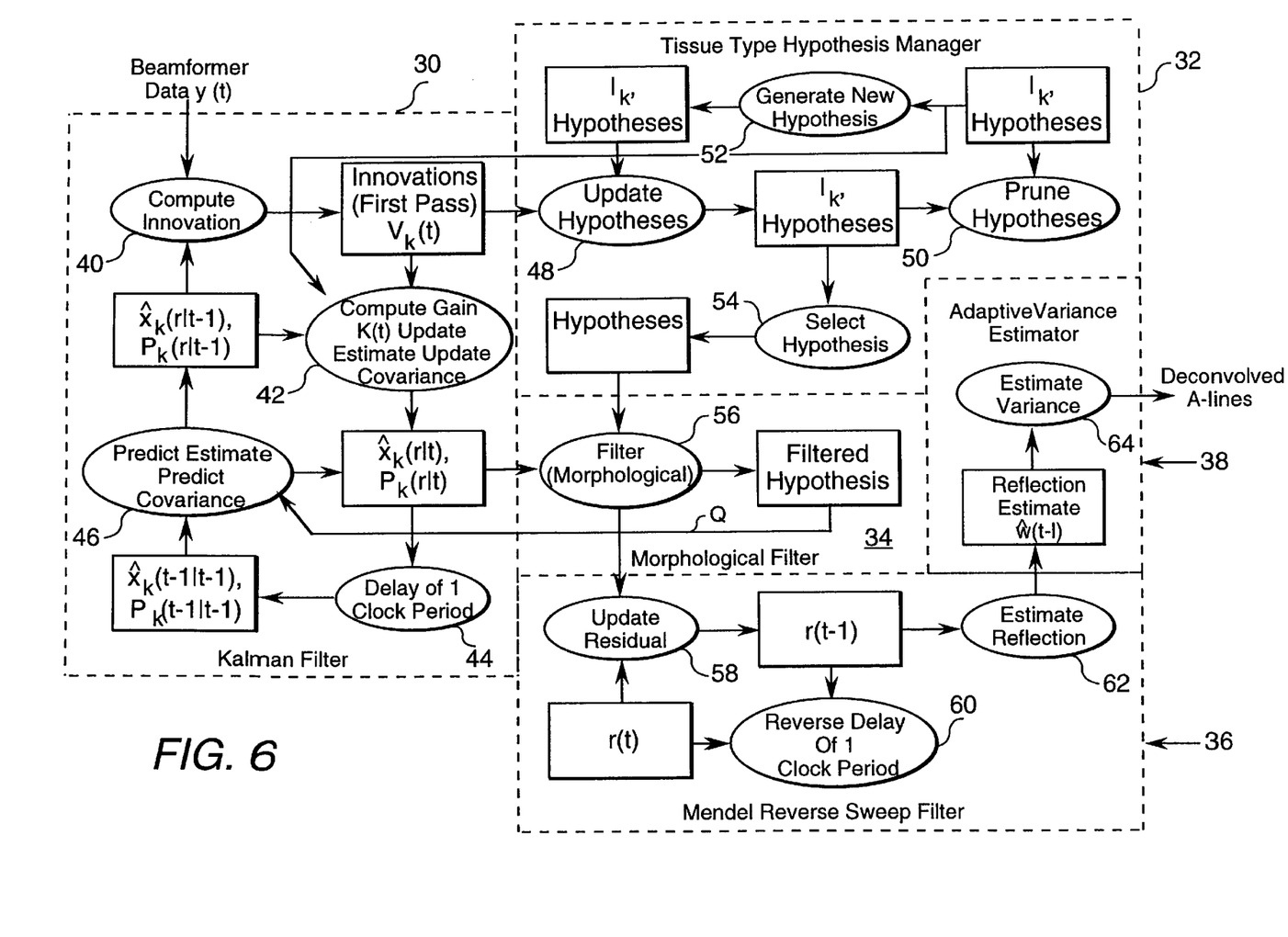
FIG. 6 is a flowchart showing the operations performed by the optimal detector components depicted in FIG. 5.

The optimal estimation algorithm in accordance with a preferred embodiment of the invention is depicted in detail in FIG. 6, with steps represented by ovals and the results of steps represented by rectangles. Each time a new beamformer measurement $y(t)$ is supplied to Kalman filters 30, a new set of hypotheses are generated by tissue type hypothesis manager 32. Specifically, as each new beamformer measurement arrives, the Kalman filters update the likelihoods corresponding to each of the hypotheses currently being maintained by the tissue type hypothesis manager 32, using Eqs. (8) and (11). The hypotheses are then rank ordered at step 48 according to the values of their likelihoods, and a fixed number K of the hypotheses having the highest likelihood values are kept, whereas the others are discarded, i.e., pruned, at step 50. That decision is then communicated to Kalman filter 30 which, at step 42, updates the state estimates and covariances. The K hypotheses of highest likelihood are then used at step 52 to generate NK new hypotheses, where N is the number of states. This cycle is repeated when the next beamformer measurement arrives.

After all the beamformer samples for a given A-line have been processed, the best tissue type hypothesis is stored at step 54. After all A-lines have been processed, the set of "best" hypotheses is passed to morphological filter 34.

In accordance with a preferred embodiment, two-dimensional continuity in the tissue type estimates is maintained. The Markov and Semi-Markov models for tissue type variation enforce continuity axially but, because A-lines are initially processed independently, there are sometimes spurious errors in the lateral direction. These errors can be eliminated to a large extent at step 56 by morphological filtering (see, e.g., Maragos et al., "Morphological filters, Part 1: Their Set-Theoretic Analysis And Relations To Linear Shift Invariant Filters, and Part 2: Their Relations To Median, Order-Statistic, And Stack Filters," IEEE Trans. Acoust., Speech, Sig. Proc., Vol. 35, No. 8, pp. 1153–1184 (1987)) of the tissue type estimates. This provides a new set of tissue type estimates, defined as a function of depth and A-line, which can then be used to derive the state-space parameters $A(t)$, $B(t)$, $C(t)$ and $Q(t)$ for each A-line. Having done so, the beamformer measurements are re-processed with Kalman filter 30 and reverse sweep Mendel filter 36 to produce a final set of reflection sequence estimates that correspond to the two-dimensional correlation structure in tissue type.

More specifically, Kalman filter innovations and likelihoods for each hypothesis are used in the reverse sweep of Mendel's algorithm to either compute the reflection sequence estimate at step 62 corresponding to the hypothesis selected at step 54 or to compute a weighted sum of estimates corresponding to the available K hypotheses.

After computing the reflection sequence estimates, an image comparable to a B-scan is generated at step 64 by computing the corresponding sample variance. The resulting image has statistics which are quite similar to those obtained by envelope detecting the beamformer signal and, as a result, is acceptable to clinicians, who have become accustomed to the Rayleigh statistics generally present in B-scan imagery.

The invention utilizes the algorithm described by Mendel et al. In "New Fast Optimal White Noise Estimators For Deconvolution," cited above, for computing $E(w^{T-1}|y^T, z^{T-1})$. This algorithm has a two-sweep structure. In the forward Kalman filtering pass, the beamformer sequence $y(t)$ is used at step 40 to generate the innovations sequence $v(t)$. In the reverse pass, the innovations sequence is used at step 62 to compute the optimal estimate of the reflection sequence $w(t)$ for $t=1, 2, \ldots, T-1$.

The following discrete time Kalman filtering equations define the forward sweep of the algorithm, with Eq. (12a) corresponding to step 40 in FIG. 6; Eqs. (12b)–(12d) corresponding to step 42; and Eqs. (12e) and (12f) corresponding to step 46:

$$v(t) = y(t) - C(t)\hat{x}(t|t-1) \tag{12a}$$

$$K(t) = P(t|t-1)C^T(t)[C(t)P(t|t-1)C^T(t) + R(t)]^{-1} \tag{12b}$$

$$\hat{x}(t|t) = \hat{x}(t|t-1) + K(t)v(t) \tag{12c}$$

$$P(t|t) = [I - K(t)C(t)]P(t|t-1) \tag{12d}$$

$$\hat{x}(t+1|t) = A(t)\hat{x}(t|t) \tag{12e}$$

$$P(t+1|t) = A(t)P(t|t)A^T(t) + B(t)Q(t)B^T(t) \tag{12f}$$

with initial conditions $\hat{x}(1|0)$ and $P(1|0)$ which, in a preferred embodiment, are both equal to zero because Eq. (2) makes an initial rest assumption. Step 44 introduces a delay of one clock period.

The following equations define the reverse sweep of Mendel's algorithm, with Eqs. (13a) and (13b) corresponding to step 58 in FIG. 5; and Eq. (13c) corresponding to step 62:

$$D(t+1)=[I-K(t+1)C(t+1)]A^T(t+1)^T \quad (13a)$$

$$r(t)=D(t+1)r(t+1)+C(t+1)\times[C(t+1)P(t+1|t)C^T(t+1) \\ +R(t+1)]^{-1}v(t+1) \quad (13b)$$

$$\hat{w}(t)=Q(t)B^T(t)r(t) \quad (13c)$$

with the initial condition r(T)=0. Step 60 in FIG. 5 is a reverse delay of one clock period.

Using results from linear estimation theory, it can be shown that the innovations process v(t) is white and is equivalent to the measurement process y(t) in the sense that the best estimate of w(t) given y(τ), τ=1, 2, . . . , T, is the same as the best estimate of w(t) given v(τ), τ=1, 2, . . . , T. The reason for transforming y(t) into v(t) and using the innovations to compute the reflection sequence estimates is that, because the innovations are white, this is much easier than computing the estimates from the beamformer measurements directly.

Furthermore, the algorithm of in FIG. 6 is a smoothing algorithm in the sense that all of the measurements (i.e., y(τ), τ=1, 2, . . . , T) are used to compute the best estimate of w(t) as opposed to a filtering algorithm in which only measurements up to time t(y(τ), τ=1, 2, . . . , t) would be used. In fact, filtering would not make much sense in this application, because y(τ), τ=1, 2, . . . , t, are uncorrelated with w(t), and hence contain no information about w(t). This is not an artifact of the model—the physical reason for this is that the imaging system is causal in the sense that reflections from depth d are not received at the beamformer until time $2d/v_s$, where $v_s$ is the speed of sound in the tissue, and hence beamformer measurements before time $2d/v_s$ cannot carry information about the reflection sequence from beyond depth d.

The algorithm involves intermediate calculation of many parameters (e.g., P(t|t), P(t|t−1), K(t) and D(t)), all of which can be computed based on knowledge of A(t), B(t), C(t), Q(t) and R(t), which are computed using the tissue state sequence and prior information or experimental data on the additive noise levels.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A system for imaging flow of ultrasound scatterers, comprising:

an ultrasound transducer array for transmitting a multiplicity of ultrasound beams in a scan plane and, for each beam, detecting reflected ultrasound echoes;

a beamformer coupled to said ultrasound transducer array for acquiring a respective A-line comprising a sequence of reflection data samples for each ultrasound beam;

means for computing a greatest-likelihood tissue type sequence estimate representing discrete states for each A-line;

means for computing a reflection sequence estimate for each A-line as a function of a respective one of the greatest-likelihood tissue type sequence estimates;

an adaptive variance estimator for computing a respective variance sequence estimate for each A-line from a respective one of said reflection sequence estimates to produce respective deconvolved A-lines; and means for displaying said deconvolved A-lines.

2. The system as defined in claim 1, wherein said means for computing a greatest-likelihood tissue type sequence estimate comprise:

Kalman filtering means for computing innovations for each A-line independently; and means for computing likelihoods of tissue type sequence hypotheses as a function of said innovations and for selecting one or more tissue type sequence hypotheses having the greatest likelihoods for each A-line to form said greatest-likelihood tissue type sequence estimates.

3. The system as defined in claim 2, further comprising means (34) for morphological filtering said greatest-likelihood tissue type sequence estimates as a function of depth and A-line to form morphologically filtered greatest-likelihood tissue type sequence estimates.

4. The system as defined in claim 2, wherein the means for computing likelihood of tissue type sequence hypotheses and for selecting one or more tissue type sequence hypotheses comprise means for generating, updating and pruning a respective set of tissue type sequence hypotheses for each A-line; and said Kalman filtering means are adapted to compute a respective set of innovations for each reflection data sample of each A-line, each innovation for a given A-line being a function of a respective tissue type sequence hypothesis for said given A-line, wherein said means for selecting means one or more tissue type sequence hypotheses is adapted to update said respective tissue type sequence hypotheses as a function of said respective innovations and to prune out tissue type sequences hypotheses having low likelihoods for each of a multiplicity of reflection data samples of a given A-line, and to select a most likely tissue type sequence hypothesis for said given A-line, thereby forming a respective one of said greatest-likelihood tissue type sequence estimates.

5. The system as defined in claim 3, wherein said Kalman filtering means is adapted to recompute an innovation for each reflection data sample of each A-line, each recomputed innovation for a given A-line being a function of a respective most likely tissue type sequence hypothesis for said given A-line, and said means for computing a reflection sequence estimate comprises a Mendel reverse sweep filter for computing said reflection sequence estimate for each A-line as a function of said morphologically filtered greatest-likelihood tissue type sequence estimates and the recomputed innovations.

6. The system as defined in claim 1, wherein said greatest-likelihood tissue type sequence estimates are based on a Markov model of tissue type changes.

7. The system as defined in claim 1, wherein said greatest-likelihood tissue type sequence estimates are based on a Semi-Markov model of tissue type changes.

8. The system as defined in claim 1, wherein said greatest-likelihood tissue type sequence estimates comprise values of a tissue reflectivity density function Q(t).

9. A method for imaging flow of ultrasound scatterers, comprising the steps of:

transmitting a multiplicity of ultrasound beams in a scan plane;

for each beam, detecting reflected ultrasound echoes;

acquiring a respective A-line comprising a sequence of reflection data samples for each ultrasound beam;

computing a greatest-likelihood tissue type sequence estimate representing discrete states for each A-line;

computing a reflection sequence estimate for each A-line as a function of a respective one of the greatest-likelihood tissue type sequence estimates;

computing a respective variance sequence estimate for each A-line from a respective one of said reflection sequence estimates to produce respective deconvolved A-lines; and displaying said deconvolved A-lines.

10. The method as defined in claim 9, wherein the step of computing a greatest-likelihood tissue type sequence estimate comprises:

computing innovations for each A-line independently; computing likelihoods of tissue type sequence hypotheses as a function of said innovations; and selecting one or more tissue type sequence hypotheses having the greatest likelihoods for each A-line to form said greatest-likelihood tissue type sequence estimates.

11. The method as defined in claim 10 wherein the step of computing innovations for each A-line independently comprises the step of Kalman filtering each A-line independently.

12. The method as defined in claim 10, further comprising the step of morphological filtering said greatest-likelihood tissue type sequence estimates as a function of depth and A-line to form morphologically filtered greatest-likelihood tissue type sequence estimates.

13. The method as defined in claim 10, wherein the selecting step comprises the steps of generating, updating and pruning a respective set of tissue type sequence hypotheses for each A-line; the step of computing innovations for each A-line independently comprises computing a respective set of innovations for each reflection data sample of each A-line, each innovation for a given A-line being a function of a respective tissue type sequence hypothesis for said given A-line; and the selecting step comprises updating said respective tissue type sequence hypotheses as a function of said respective innovations, pruning out tissue type sequences hypotheses having low likelihoods for each of a multiplicity of reflection data samples of a given A-line, and selecting a most likely tissue type sequence hypothesis for said given A-line, thereby forming a respective one of said greatest-likelihood tissue type sequence estimates.

14. The method as defined in claim 11, further comprising the step of morphological filtering said greatest-likelihood tissue type sequence estimates as a function of depth and A-line to form morphologically filtered greatest-likelihood tissue type sequence estimates.

15. The method as defined in claim 14, further comprising the steps of recomputing an innovation for each reflection data sample of each A-line by performing Kalman filtering, each recomputed innovation for a given A-line being a function of a respective most likely tissue type sequence hypothesis for said each A-line, wherein the step of computing a reflection sequence estimate comprises performing Mendel reverse sweep filtering to compute said reflection sequence estimate for each A-line as a function of said morphologically filtered greatest-likelihood tissue type sequence estimates and said recomputed innovations.

16. The method as defined in claim 9, wherein said greatest-likelihood tissue type sequence estimates are based on a Markov model of tissue type changes.

17. The method as defined in claim 9, wherein said greatest-likelihood tissue type sequence estimates are based on a Semi-Markov model of tissue type changes.

18. The method as defined in claim 9, wherein said greatest-likelihood tissue type sequence estimates comprise values of a tissue reflectivity density function $Q(t)$.

19. A system for imaging flow of ultrasound scatterers, comprising:

an ultrasound transducer array transmitting a multiplicity of ultrasound beams in a scan plane and, for each beam, detecting reflected ultrasound echoes;

means coupled to said ultrasound transducer array for acquiring a respective A-line comprising a sequence of reflection data samples for each ultrasound beam;

means computing a greatest-likelihood tissue type sequence estimate representing discrete states for each A-line;

means convolving each A-line as a function of a respective one of the greatest-likelihood tissue type sequence estimates; and means for displaying said deconvolved A-lines.

20. The system as defined in claim 19, wherein said means for computing a greatest-likelihood tissue type sequence estimate comprise:

Kalman filtering means for computing innovations for each A-line independently; and means for computing likelihoods of tissue type sequence hypotheses as a function of said innovations and for selecting one or more tissue type sequence hypotheses having the greatest likelihoods for each A-line to form said greatest-likelihood tissue type sequence estimates.

21. The system as defined in claim 20, further comprising means for morphological filtering said greatest-likelihood tissue type sequence estimates as a function of depth and A-line to form morphologically filtered greatest-likelihood tissue type sequence estimates.

22. The system as defined in claim 21, wherein said Kalman filtering means is adapted to recompute an innovation for each reflection data sample of each A-line, each recomputed innovation for a given A-line being a function of a respective most likely tissue type sequence hypothesis for said given A-line, and said deconvolving means comprises a Mendel reverse sweep filter (36) for computing a reflection sequence estimate for each A-line as a function of said morphologically filtered greatest-likelihood tissue type sequence estimates and the recomputed innovations.

23. The system as defined in claim 19, wherein said greatest-likelihood tissue type sequence estimates are based on a Markov model of tissue type changes.

24. The system as defined in claim 19, wherein said greatest-likelihood tissue type sequence estimates are based on a Semi-Markov model of tissue type changes.

25. The system as defined in claim 19, wherein said greatest-likelihood tissue type sequence estimates comprise values of a tissue reflectivity density function $Q(t)$.

26. The system as defined in claim 22 wherein said deconvolving means further includes an adaptive variance estimator for computing a variance estimate from each reflection sequence estimate to form respective deconvolved A-lines.

* * * * *